US008066939B2

(12) United States Patent
Elrod

(10) Patent No.: US 8,066,939 B2
(45) Date of Patent: Nov. 29, 2011

(54) DESCENTING METHODS

(75) Inventor: Scott A. Elrod, Angleton, TX (US)

(73) Assignee: Parah, LLC, Angleton, TX (US)

( * ) Notice: Subject to any disclaimer, the term of this patent is extended or adjusted under 35 U.S.C. 154(b) by 0 days.

(21) Appl. No.: 12/660,347

(22) Filed: Feb. 24, 2010

(65) Prior Publication Data
US 2010/0226819 A1 Sep. 9, 2010

Related U.S. Application Data

(60) Division of application No. 11/714,083, filed on Mar. 5, 2007, now abandoned, which is a continuation-in-part of application No. 11/018,620, filed on Dec. 21, 2004, now Pat. No. 7,939,015.

(51) Int. Cl.
*A61L 9/00* (2006.01)
(52) U.S. Cl. ............... 422/5; 422/120; 422/123
(58) Field of Classification Search .............. 422/5, 120, 422/123, 186.07
See application file for complete search history.

(56) References Cited

U.S. PATENT DOCUMENTS

| | | | |
|---|---|---|---|
| 1,961,878 A | 6/1934 | Gilkey | 423/210 X |
| 2,203,188 A | 6/1940 | Beer | |
| 3,214,364 A | 10/1965 | Van Tuyle et al. | |
| 3,421,836 A | 1/1969 | Sundin et al. | |
| 3,601,292 A | 8/1971 | Bliss | |
| 3,670,425 A | 6/1972 | Benjamin | |
| 3,750,556 A | 8/1973 | Duke | 454/159 |
| 3,937,967 A | 2/1976 | Steinitz | 250/435 |
| 3,949,056 A | 4/1976 | Nakshbendi | 423/210 |
| 4,045,316 A | 8/1977 | Legan | 204/157.3 |
| 4,238,857 A | 12/1980 | Waters | 2/171.3 |
| 4,309,388 A | 1/1982 | Tenney et al. | 422/304 |
| 4,374,571 A | 2/1983 | Hirvela | |
| 4,735,010 A | 4/1988 | Grinarml | |
| 4,811,159 A | 3/1989 | Foster, Jr. | 361/231 |
| 4,863,687 A | 9/1989 | Stevens et al. | 422/4 |
| 4,867,052 A | 9/1989 | Cipelletti | 99/451 |
| 4,904,289 A | 2/1990 | Miyakami et al. | 62/157 |
| 4,941,270 A | 7/1990 | Hoffman | 34/60 |
| 4,953,674 A | 9/1990 | Landes | 190/108 |
| 4,990,311 A | 2/1991 | Hirai et al. | 422/4 |
| 5,087,426 A | 2/1992 | Inoue et al. | 422/123 |
| 5,152,077 A | 10/1992 | Liang | |
| 5,185,129 A | 2/1993 | Koutrakis et al. | 422/88 |
| 5,192,500 A | 3/1993 | Treddenick | 422/56 |
| 5,303,496 A | 4/1994 | Kowalkowski | |

(Continued)

FOREIGN PATENT DOCUMENTS
EP   0261987   3/1988
(Continued)

OTHER PUBLICATIONS

English abstract for JP 06-327749 A, inventor: Masuda, 1994.*

(Continued)

*Primary Examiner* — Sean E Conley
(74) *Attorney, Agent, or Firm* — Holland & Hart

(57) ABSTRACT

The present invention, in certain aspects, discloses systems and methods for treating a human being and/or items with descenting material, the systems, in certain aspects, including a generator for producing descenting material, and, in certain aspects at least one direction apparatus in communication with the generator for receiving produced descenting material from the generator and for directing said descenting material in a desired direction.

38 Claims, 5 Drawing Sheets

U.S. PATENT DOCUMENTS

| | | | |
|---|---|---|---|
| 5,316,182 A | 5/1994 | Lee et al. | 227/78 |
| 5,342,415 A | 8/1994 | Wasinger et al. | |
| 5,383,236 A | 1/1995 | Sesselmann | 2/243.1 |
| 5,429,271 A | 7/1995 | Porter | |
| 5,433,230 A | 7/1995 | Miller | 134/110 |
| 5,433,919 A | 7/1995 | Baltes | 422/1 |
| 5,457,054 A | 10/1995 | Geisinger et al. | |
| 5,468,454 A | 11/1995 | Kim | 422/121 |
| 5,484,472 A | 1/1996 | Weinberg | 96/26 |
| 5,514,345 A | 5/1996 | Garbutt et al. | 422/124 |
| 5,520,893 A | 5/1996 | Kasting, Jr. et al. | 422/305 |
| 5,539,930 A | 7/1996 | Sesselmann | 2/243.1 |
| 5,547,476 A | 8/1996 | Siklosi et al. | 8/142 |
| 5,667,564 A | 9/1997 | Weinberg | 96/58 |
| 5,681,355 A | 10/1997 | Davis et al. | 8/137 |
| 5,762,648 A | 6/1998 | Yeazell | 8/137 |
| 5,766,560 A | 6/1998 | Cole | 422/186 |
| 5,789,368 A | 8/1998 | You et al. | 510/297 |
| 5,790,987 A | 8/1998 | Sesselmann | 2/243.1 |
| 5,795,544 A | 8/1998 | Matz | |
| 5,833,740 A | 11/1998 | Brais | |
| 5,835,840 A | 11/1998 | Goswami | 422/186.3 |
| 5,891,391 A | 4/1999 | Fore | 422/5 |
| 5,911,957 A | 6/1999 | Khatchatrian et al. | 422/186 |
| 5,931,014 A | 8/1999 | Cole | 62/264 |
| 5,942,438 A | 8/1999 | Antonoplos et al. | |
| 5,983,834 A | 11/1999 | Tai | 119/448 |
| 6,007,770 A | 12/1999 | Peiper et al. | 422/22 |
| 6,009,559 A | 1/2000 | Sesselmann | 2/243.1 |
| 6,074,608 A | 6/2000 | Matz | |
| 6,094,549 A | 7/2000 | Hiraoka et al. | 399/93 |
| 6,134,718 A | 10/2000 | Sesselmann | 2/243.1 |
| 6,134,806 A | 10/2000 | Dhaemers | 34/404 |
| 6,149,038 A | 11/2000 | Tsai | 223/86 |
| 6,153,111 A | 11/2000 | Conrad et al. | 210/741 |
| 6,156,268 A | 12/2000 | Curry et al. | 422/4 |
| 6,163,098 A | 12/2000 | Taylor et al. | 310/308 |
| 6,182,671 B1 | 2/2001 | Taylor et al. | |
| 6,218,189 B1 | 4/2001 | Antonoplos et al. | |
| 6,267,242 B1 | 7/2001 | Nagata et al. | |
| 6,284,204 B1 | 9/2001 | Cole et al. | 422/186 |
| 6,312,507 B1 | 11/2001 | Taylor et al. | 96/19 |
| 6,336,964 B1 | 1/2002 | Omatsu et al. | 106/31.44 |
| 6,340,447 B2 | 1/2002 | Johnson | 422/5 |
| 6,355,216 B1 | 3/2002 | Kristiansson et al. | 422/29 |
| 6,368,867 B1 | 4/2002 | Gibson et al. | |
| 6,379,435 B1 | 4/2002 | Fukunaga et al. | 96/111 |
| 6,503,547 B1 | 1/2003 | Lima | 426/231 |
| 6,564,591 B2 | 5/2003 | Noyes et al. | 68/5 C |
| 6,565,805 B2 | 5/2003 | Khatchatrian et al. | 422/28 |
| 6,576,190 B1 | 6/2003 | Park | 422/28 |
| 6,613,277 B1 | 9/2003 | Monagan | 422/24 |
| 6,630,105 B1 | 10/2003 | O'Neill et al. | |
| 6,632,407 B1 | 10/2003 | Lau et al. | 422/186 |
| 6,635,439 B2 | 10/2003 | Morrison et al. | |
| D486,357 S | 2/2004 | Leba et al. | D7/605 |
| 6,790,411 B1 | 9/2004 | Read | |
| 6,896,853 B2 | 5/2005 | Lau et al. | 422/186 |
| 6,967,008 B1 | 11/2005 | Barnes | |
| 7,117,687 B2 | 10/2006 | Naaman | 62/259.3 |
| 7,118,608 B2 | 10/2006 | Lovell | 55/385.1 |
| 7,186,373 B2 | 3/2007 | Centanni | |
| 7,222,634 B2 | 5/2007 | Hess et al. | 135/93 |
| 7,662,636 B2 | 2/2010 | Maruo et al. | |
| 2002/0030022 A1 | 3/2002 | Bradley | 210/752 |
| 2002/0071795 A1 | 6/2002 | Jensen | |
| 2002/0094298 A1 | 7/2002 | Monagan | |
| 2003/0044308 A1 | 3/2003 | Toth | 422/5 |
| 2003/0066767 A1 | 4/2003 | Felsenthal | |
| 2003/0089010 A1 | 5/2003 | Wechter et al. | |
| 2003/0111435 A1 | 6/2003 | Chen | |
| 2004/0002349 A1 | 1/2004 | Yamagishi et al. | 455/456.3 |
| 2004/0047775 A1 | 3/2004 | Lau et al. | |
| 2004/0149329 A1 | 8/2004 | Hess et al. | |
| 2004/0163184 A1 | 8/2004 | Waldron et al. | |
| 2004/0221396 A1 | 11/2004 | Johnson | |
| 2005/0186108 A1 | 8/2005 | Fields | |
| 2005/0207951 A1 | 9/2005 | Lee et al. | 422/186.07 |
| 2006/0006122 A1 | 1/2006 | Burns et al. | |
| 2006/0096331 A1 | 5/2006 | Kim | 68/5 C |
| 2007/0092414 A1 | 4/2007 | Malyon | 422/186.3 |
| 2007/0166186 A1 | 7/2007 | Stec | 422/5 |
| 2007/0212253 A1 | 9/2007 | Elrod | 422/5 |
| 2008/0036594 A1 | 2/2008 | Kates | |
| 2010/0071633 A1 | 3/2010 | Elrod | 119/712 |
| 2010/0107991 A1 | 5/2010 | Elrod et al. | 119/712 |
| 2010/0289655 A1 | 11/2010 | Elrod et al. | |

FOREIGN PATENT DOCUMENTS

| | | | |
|---|---|---|---|
| JP | 06-327749 A | * | 11/1994 |
| JP | 09239018 A | | 9/1997 |
| JP | 09262141 A | | 10/1997 |
| JP | 1109948 A | | 1/1999 |
| JP | 11009949 A | | 1/1999 |
| JP | 11226106 A | | 8/1999 |
| JP | 11226108 A | | 8/1999 |
| JP | 2003001237 A | | 1/2003 |
| JP | 2003024426 A | | 1/2003 |
| WO | WO 0151096 | | 1/2001 |
| WO | WO 03089017 | | 4/2003 |
| WO | WO 2004/067043 | | 8/2004 |
| WO | WO 2005077425 A1 | | 2/2005 |
| WO | 2005021135 | | 3/2005 |

OTHER PUBLICATIONS

U.S. Appl. No. 11/018,620, filed Dec. 21, 2004, Elrod.

McElhiney et al, Dec. 2003, Detection of the cyanobacterial hepatoxins microcystins; in Toxicology & Applied Pharmacology, pp. 219-230.

Fehrenbacher, Jill, Robotic Pollution-Sniffing Eco Dogs! [on-line], Feb. 26, 2007; retrieved from the internet: URL: http://inhabitat.com/robotic-pollution-sniffing-eco-dogs/.

Bomms Terminator, Game Finder, May 24, 2002.

Terminator 800, Game Finder, Feb. 13, 2003.

Bomms Terminator. Game Finder—Outdoor Enhancement Systems, Web page print outs from http://www.game-finder.com/bomms-terminator.aspx, printed on Dec. 23, 2006 (2 pages). [cited in PCT/US2005/004322].

English machine translation of JP 2003024426, date of publication of application is Jan. 28, 2003 (12 pages).

English Abstract for JP 06 327749A, Inventor: Masuda, date of publication of application is Nov. 29, 1994 (12 pages).

Provisional U.S. Appl. No. 60/543,505, filed Feb. 11, 2004 (1 page).

* cited by examiner

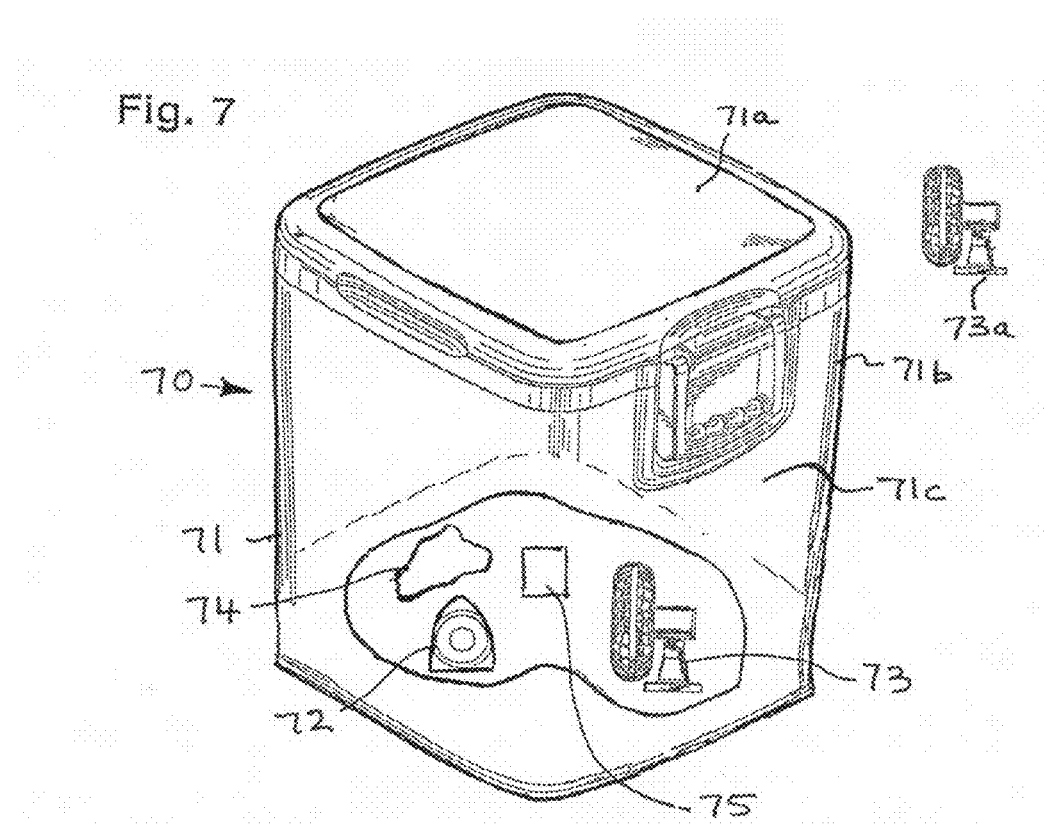
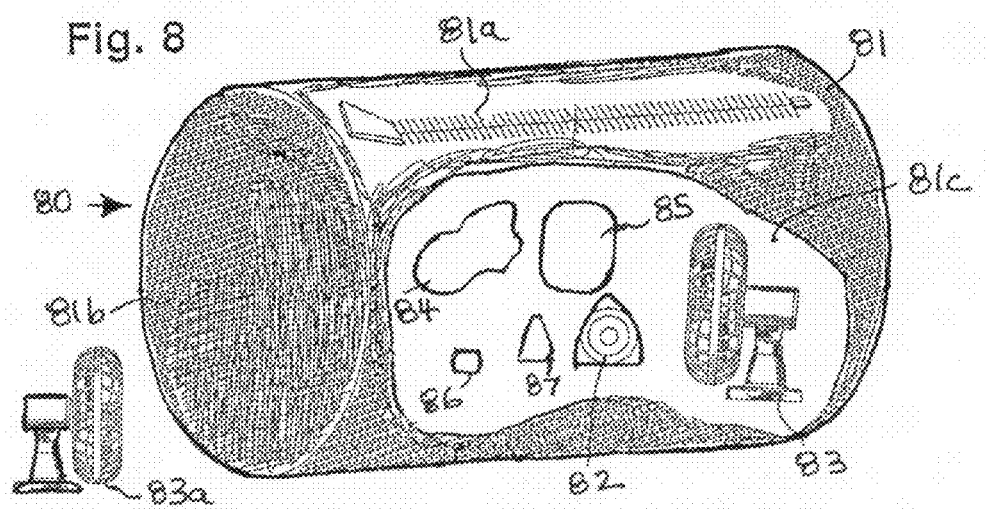

DESCENTING METHODS

CROSS-REFERENCE TO RELATED APPLICATIONS

This application is a division of U.S. application Ser. No. 11/714,083 filed Mar. 5, 2007 now abandoned which is a continuation-in-part of U.S. patent application Ser. No. 11/018,620 filed Dec. 21, 2004, now U.S. Pat. No. 7,939,015 B1, said applications co-owned with the present invention and both incorporated fully herein for all purposes and from which applications the present invention and application claim priority under the Patent Laws.

BACKGROUND OF THE INVENTION

1. Field of the Invention

The present invention is directed to descenting systems and methods; in certain aspects, to such systems and methods for facilitating human/animal encounters and activities; and in other aspects to methods and systems for reducing or eliminating human odors that are detectable by animals. The invention relates to a method of descenting the clothes and apparatus of sportsmen, both professional, non professional, military personnel, bikers, campers and the like. In certain aspects a method is provided for reducing or removing human scent and any other scent that is not advantageous in an environment from clothing and equipment of hunters and fish odors from fishermen utilizing an oxidizing agent which is ozone and/or a combination of hydroxyl and hydroperoxide ions. More particularly, there is provided a method of reducing or removing human scent and any other scent in a space between a human and an animal that is not advantageous in an environment, including scents emitting from human breath, human bodies, and from clothing and equipment, the methods utilizing an oxidizing agent which is, e.g., ozone and/or a combination of hydroxyl and hydroperoxide ions.

2. Description of Related Art

The prior art discloses a variety of descenting (removal of scents) apparatus and methods, examples of which (and not by way of limitation) are found in U.S. Pat. Nos. 4,309,388; 4,867,052; 4,941,270; 5,087,426; 5,433,919; 5,468,454; 5,484,472; 5,514,345; 5,539,930; 5,547,476; 5,667,564; 5,681,355; 5,762,648; 5,766,560; 5,789,368; 5,790,987; 5,911,957; 5,931,014; 6,007,770; 6,009,559; 6,134,806; 6,134,718; 6,149,038; 6,156,268; 6,163,098; 6,284,204; 6,312,507; 6,355,216; 6,379,435; 6,503,547; 6,564,591; 6,565,805; and 6,576,190, and published U.S. patent application 2003/0044308—all of which are incorporated fully herein for all purposes.

Hunters, wildlife enthusiasts, and wildlife photographers all have an interest in attracting wildlife, such as, but not limited to, deer; and/or an interest in not being detected by animals. Deer rely heavily on their sense of smell to react with their surrounding environment, including to sense danger, interact with other deer and find food. Scents that are not a natural part of the environment will often function as a warning to deer, which may result in the deer being spooked and running from the unnatural scent.

According to Bernier et al in Analytical Chemistry, 2000, volume 72, issue 4, pages 747-756 and references cited therein which are incorporated fully herein by reference, as many as 346 discernible compounds were identified in human skin emanations. The majority of these were carboxylic acids, alcohols and esters, but aldehydes, aromatics, heterocyclics, ketones, sulfides and thio compounds were also identified. Work cited in Bernier has identified over 100 compounds from human breath. Work cited in Bernier identified foot odor as another source of odor. Some of these compounds are the result of bacteria reacting with body emanations, while other compounds directly emanate from humans. Other compounds emanated from humans can include pheromones, deodorants and perfumes as well as the detergents, perfumes, scents, and additives left on human clothes. While it is not known which specific compound or blends of compounds emanating from humans are identified by an animal as human, there is currently no effective way to eliminate or reduce odors from humans and from clothing and equipment enough to reduce the odors to inhibit detection by wildlife or effectively attract wildlife.

Persons interested in preventing detection by deer detecting human odors or interested in attracting deer often use masks, attractants, or cover scents to prevent alerting and spooking the deer. Some commonly used masks are carbon sprays which, in addition to being dangerous to inhale and which can irritate skin, become ineffective once dry. Many of the attractants contain deer urine or estrous, which besides being offensive to the human user, have limited shelf life and are generally ineffective since especially the estrous tend to occur naturally only in certain seasons. Cover scents such as fruit extracts or fragrances last a short time and are often so over-powering that the deer easily identifies the smell as unnatural and runs. The use of descenting soaps and shampoos is messy, time-consuming, often skin irritating, often ineffective and does not address breath odor. Breath descenting using herbs are generally distasteful, and face masks containing carbons or sieves are extremely uncomfortable.

More recently, the use of clothing containing activated carbons and/or clothing containing bacteria killing metals such as silver has gained some popularity. However, activated carbon has a very low capacity for odorants and requires temperatures preferably above 400° C., more preferably above 600° C. to regenerate the carbon. These temperatures are well beyond temperature (100 C to 120 C) that a conventional gas or electric clothes dryer is capable of achieving. Placement of clothing in ovens capable of achieving 400 C plus temperatures needed to regenerate the carbon can damage the fabric of a garment. Silver or other metal-containing clothing requires direct contact of the metal with the bacteria to be effective, which is almost never the case since the clothing would then be so restricting as to be uncomfortable. These types of clothing are also expensive and do not address human odors such as those in human breath, nor do they address any of the odors emanating from the foot or any exposed part of the skin like the head and hands.

It has now been discovered that gaseous ozone effectively kills bacteria and reduces or eliminates odors emanating from humans as well as odors contained in clothing worn by hunters. The advantages of ozone over other known masking and descenting methods include the facts that: ozone is a gas that eliminates odors emanating from a person (e.g., a hunter) and from personal equipment and can eliminate odors in a space between a person and an animal; and ozone is completely natural to the environment and leaves behind a very pleasant clean smell that wildlife and humans readily recognize, e.g. after a lightning rain. Known ozone generators include electrical discharge, UV light, and combinations thereof. The generator may be battery operated, operated with a car adaptor, and/or may be operated with AC current. The AC current may be supplied directly from an electrical outlet, or may be supplied using a portable generator.

Ozone is well known to treat odorous air, microorganisms, bacteria, mold, smoke, aromatic hydrocarbons, and volatile organic compounds (see for example U.S. Pat. Nos. 1,961, 878; 2,203,188; 3,421,836; 3,750,556; 3,937,967; 3,949,056; 4,045,316; 4,863,687; 4,904,289; 4,990,311; 5,087,426; 5,835,840; 5,983,834; 6,094,549; 6,613,277; 6,632,407; 20020030022; 20060096331; and references cited therein, which are all of which are incorporated fully herein for all purposes); and foreign references EP 261987; WO 200151096; WO 2003089017; WO 2005021135. WO 2005077425 and references cited therein, which are incorporated fully herein for all purposes, teaches the use of ozone to descent hunters clothing and other personal effects to be worn or carried on a hunting trip. In this case, the hunter, the clothing or personal effects are placed in a container, a portable enclosure, or a special descenting closet or room located, e.g., in a lodge or cabin in which the hunter is staying. As soon as the hunter leaves the building and enters a vehicle, or passes a moving vehicle, or begins to sweat, any prior descenting is of little value.

Animals have an acute sense of smell and are capable of recognizing a human scent or any other scent that is not advantageous in that environment at long distances. To avoid such recognition a hunter will attempt to stay down wind of the animal being hunted. Certain known methods used by hunters to trick animals are to mask the human odor utilizing a carbon spray or cover spray scents or an animal scent. Unfortunately the animal scents which are utilized, are obnoxious and linger on the clothing for long periods of time and often do not mask out human scents. Some of the scents utilized include animal urine. A hunter who is camping overnight does not desire the animal scents to be carried over to bedtime, home, car, etc.

There are other drawbacks in utilizing animal scents or any other scents. The scent may attract a predator of the game which the hunter is not hunting for which the hunter may not be prepared to encounter. Containers containing food, beverages, or any other substance emit scents readily recognizable to animals that may not be masked by animal scents or may not be natural to a given environment. Female hikers, campers, hunters, etc. can emit a readily recognizable scent to animals from menstruation that may not be masked by animal scents. Also, the weapon used by the hunter has an odor recognizable by some animals which cannot be disguised with a scent.

Fishermen have the problem of fish odor on their hands and clothes which is difficult to remove. For fishermen camping overnight the fish odor is not only undesirable because of the odor but can also attract animals such as bears which the fishermen is not prepared to meet.

Hunters have prepared their clothing before hand by washing to remove prior scents and/or human odor. The washing materials may also leave an odor. However, out in the field the hunter can sweat and permeate the clothing with a human scent. It would be desirable to deodorize clothing during a hunt or while on a fishing trip.

Ozone has been used for decontaminating buildings and for decolorizing denim garments. U.S. Pat. No. 5,833,740 to Brais discloses an apparatus for sterilizing bottles utilizing ozone. The reference recognizes that ozone in large quantities can be harmful or irritating. Consequently, it was necessary to provide means for decomposing the excess ozone and/or to cause its escape into the atmosphere.

Ozone is a powerful oxidizing agent. Ozone has 150% of the oxidizing potential of chlorine and twice the oxidizing potential of bromine. Ozone has been shown to be much more effective than chlorine with a reaction time up to 10 times faster. Ozone also readily self-destructs into simple diatomic oxygen due to its inherent instability. Ozone oxidizes biological products and kills bacteria.

Catalytic ionization of air using ultraviolet light is known to produce a mixture of ozone-containing hydroxyl and hydroperoxide ions. Ionization devices which are used to eliminate smoke and odors are known in the art to produce hydroxyl and hydroperoxide ions, e.g. those used in automobiles.

BRIEF SUMMARY OF THE INVENTION

The present invention, in certain aspects, is directed to systems and methods which use gaseous ozone to kill bacteria and reduce or eliminate odors emanating from humans, e.g. in breath or from skin, as well as odors in clothing worn by a person that are volatilized into the air space between the human and the wildlife to prevent wildlife from detecting the presence of humans and/or to enhance encounters with and the attraction of wildlife. One embodiment is directed to wearing or carrying a portable ozone generator while walking, waiting for, or engaging in attracting wildlife. Another embodiment is directed to wearing or carrying a portable ozone generator while engaging in an activity, e.g. walking, waiting for wildlife, or engaging in preventing wildlife from detecting the presence of humans. Another embodiment is directed to clothing incorporating or combined with ozone directing apparatus or devices. Yet another embodiment is directed to the treatment of clothing—e.g. directly with ozone, prior to or while being worn—to enhance the attraction of wildlife. Yet another embodiment is directed to the use of gaseous ozone in or around a tent, site, or blind to reduce or eliminate odors to enhance the attraction of wildlife, e.g. for hunters, wildlife enthusiasts and wildlife photographers. Yet another embodiment is directed to the use of gaseous ozone in or around a tent, site, or blind to reduce or eliminate odors to prevent the detection of humans by wildlife, e.g., for hunters, wildlife enthusiasts, and wildlife photographers.

The invention relates to a method for deodorizing the clothing and apparatus of sportsmen, professional or non professional. More particularly, there are provided methods for reducing or eliminating human scent or any other foreign scent from clothing etc.; and there are provided methods for removing human scent or any other foreign scent (collectively "foreign scents") from items and/or clothing, e.g. clothing used by hunters before or during a hunt—through the use of ozone or hydroxyl and hydroperoxide ions produced by ionization in a manner that would not cause irritation or injury to the user or equipment. Also, there is provided a method for removing fish odor from fishermen and their clothing and equipment while in the field including lures, tackle boxes and containers. The principal objective of the invention is the provision of a method for effectively removing human scent from clothing used by sportsmen.

It is yet another object of the invention to provide a method for military personnel to escape detection by other humans or by scent animals (e.g., scent dogs). In certain particular aspects the present invention provides methods for reducing or eliminating human or any other foreign scent from items, e.g. from clothing and equipment, used by military personnel desiring to evade detection or capture—through the use of ozone or ozone with hydroxyl and hydroperoxide ions produced by ionization in a manner that would not cause irritation or injury to the user or equipment.

It is another object of the invention to deodorize fish odor on fishermen.

It is yet another object of the invention to de-scent or deodorize sportsmen while out in the field by the use of ozone or hydroxyl and hydroperoxide ions.

Yet another object of the invention is to provide a method of deodorizing clothing with ozone so that it will not cause irritation or harm.

It is a further object of the invention to provide ozone in a compressed or generated form in a hand held container for application in the field by sportsmen.

Other objects and advantages of this invention will become apparent from the description of the preferred embodiments and the claims.

For safety reasons, government regulations have recommended, and sometimes regulated, the amount of ozone to which a human is to be exposed. For example, OSHA requires that employee permissible exposure limit (PEL) as an eight hour time-weighted average value of 0.1 ppm ozone in air. The OSHA short term exposure limit (STEL) is 0.3 ppm over a 15 minute period, not to be repeated more than two times in an eight hour period. Prolonged exposure of humans has produced no apparent ill effects at 0.2 ppm. In a variety of embodiments of the present invention, a human being is exposed to ozone generated by an ozone generator. In any such embodiments the human being may be limited to exposure to ozone in a concentration of 0.2 parts per million (or less). In any such embodiment, in certain aspects, in which the human being is to be exposed to ozone for a time period of up to about 8 hours (about 8 hours or less), the ozone concentration is limited to 0.1 parts per million (or less). In any such embodiment, a desired level of ozone concentration to which the human being is exposed is maintained in a space of a desired size around the human being, e.g., in certain aspects, a desired level of ozone is maintained within about a 6 foot radius of the human being (and, in one aspect, at an ozone concentration level of 0.2 ppm or less and, in another aspect, at an ozone concentration of 0.1 ppm or less).

In certain embodiments according to the present invention, clothing is treated with ozone so that ozone is retained on the clothing, e.g. for several hours and, in certain aspects, for up to 24 hours, and in other embodiments for more than 24 hours. Ozone retained on the clothing continues to descent scents which come in contact with the ozone. A variety of cloths, including, but not limited to knits, fleeces, cotton cloth, cotton blended cloth, fibrous cloth, and rough cloths have retained ozone. In other embodiments treatment with ozone temporarily changes the color of colored cloth and then, after some time period, the cloth returns to its original color. This color change indicates that an item of clothing has been treated with ozone; that it is retaining some ozone thereon; and the change back to an original color indicates ozone is no longer being retained on the clothing. "Color" refers to any color (e.g., but not limited to, white, red, green, blue, yellow, orange, violet, black, purple, brown, etc.)

Accordingly, the present invention includes features and advantages which are believed to enable it to advance descenting technology. Characteristics and advantages of the present invention described above and additional features and benefits will be readily apparent to those skilled in the art upon consideration of the following detailed description of preferred embodiments and referring to the accompanying drawings.

What follows are some of, but not all, the objects of this invention. In addition to the specific objects stated below for at least certain preferred embodiments of the invention, there are other objects and purposes which will be readily apparent to one of skill in this art who has the benefit of this invention's teachings and disclosures. It is, therefore, an object of at least certain preferred embodiments of the present invention to provide:

New, useful, unique, efficient, nonobvious methods and systems for enhancing encounters with or the attraction of animals;

Such systems and methods including the treatment of clothing and other items with ozone;

Such systems and methods including wearing ozone-directing apparatuses; and

New useful, unique, efficient, nonobvious systems and methods for reducing foreign scent in a space between a human being and an animal.

Certain embodiments of this invention are not limited to any particular individual feature disclosed here, but include combinations of them distinguished from the prior art in their structures, functions, and/or results achieved. Features of the invention have been broadly described so that the detailed descriptions that follow may be better understood, and in order that the contributions of this invention to the arts may be better appreciated. There are, of course, additional aspects of the invention described below and which may be included in the subject matter of the claims to this invention. Those skilled in the art who have the benefit of this invention, its teachings, and suggestions will appreciate that the conceptions of this disclosure may be used as a creative basis for designing other structures, methods and systems for carrying out and practicing the present invention. The claims of this invention are to be read to include any legally equivalent devices or methods which do not depart from the spirit and scope of the present invention.

The present invention recognizes and addresses the previously-mentioned problems and long-felt needs and provides a solution to those problems and a satisfactory meeting of those needs in its various possible embodiments and equivalents thereof. To one of skill in this art who has the benefits of this invention's realizations, teachings, disclosures, and suggestions, other purposes and advantages will be appreciated from the following description of certain preferred embodiments, given for the purpose of disclosure, when taken in conjunction with the accompanying drawings. The detail in these descriptions is not intended to thwart this patent's object to claim this invention no matter how others may later disguise it by variations in form, changes, or additions of further improvements.

The Abstract that is part hereof is to enable the U.S. Patent and Trademark Office and the public generally, and scientists, engineers, researchers, and practitioners in the art who are not familiar with patent terms or legal terms of phraseology to determine quickly from a cursory inspection or review the nature and general area of the disclosure of this invention. The Abstract is neither intended to define the invention, which is done by the claims, nor is it intended to be limiting of the scope of the invention in any way.

It will be understood that the various embodiments of the present invention may include one, some, or all of the disclosed, described, and/or enumerated improvements and/or technical advantages and/or elements in claims to this invention.

BRIEF DESCRIPTION OF THE SEVERAL VIEWS OF THE DRAWING

A more particular description of embodiments of the invention briefly summarized above may be had by references to the embodiments which are shown in the drawings which form a part of this specification. These drawings illustrate certain preferred embodiments and are not to be used to improperly limit the scope of the invention which may have other equally effective or legally equivalent embodiments.

FIG. 7 is a perspective view, partially cutaway, of a system useful in methods according to the present invention.

FIG. 8 is a perspective view, partially cutaway, of a system useful in methods according to the present invention.

Figure 1:
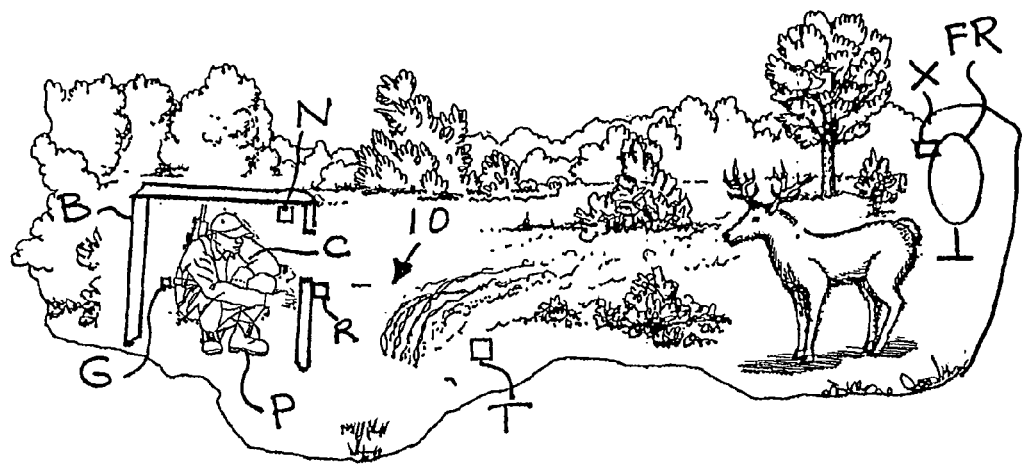
FIG. 1 is a perspective view showing use of systems according to the present invention.

Presently preferred embodiments of the invention are shown in the above-identified figures and described in detail below. It should be understood that the appended drawings and description herein are of preferred embodiments and are not intended to limit the invention or the appended claims. On the contrary, the intention is to cover all modifications, equivalents and alternatives falling within the spirit and scope of the invention as defined by the appended claims. In showing and describing the preferred embodiments, like or identical reference numerals are used to identify common or similar elements. The figures are not necessarily to scale and certain features and certain views of the figures may be shown exaggerated in scale or in schematic in the interest of clarity and conciseness. [0i]

As used herein and throughout all the various portions (and headings) of this patent, the terms "invention", "present invention" and variations thereof mean one or more embodiment, and are not intended to mean the claimed invention of any particular appended claim(s) or all of the appended claims. Accordingly, the subject or topic of each such reference is not automatically or necessarily part of, or required by, any particular claim(s) merely because of such reference.

DETAILED DESCRIPTION OF THE INVENTION

"Person" as used herein includes, but is not limited to, "hunter" and a "hunter" is defined as including hunters of wild game and other animals and also includes nature enthusiasts, trappers, military personnel, military personnel seeking to evade others and/or avoid capture, hikers, fishermen and fisherwomen, backpackers, and photographers; and "hunt" or "hunting" is defined as including the hunting of wild game and other animals for the purposes of encountering, attracting, avoiding, escaping from, photographing, avoiding detection by, capturing, killing and/or observing them. "An animal" as used herein includes, but is not limited to, any small or large game animal including deer, elk, sheep, pig, moose, caribou, bird, rabbit, elephant, mountain lions, bear and fish, and combinations thereof and, in certain aspects, "animal" includes human beings. For example, a human may desire to prevent the detection of human body odors or odors resulting from the human consumption of various foods and/or spices (e.g., pepper or curry) and/or beverages by the human himself or herself or by another human. A "blind" as used herein includes any natural or man-made place of observing, hiding and/or protecting a person including, but not limited to, a tent, shack, tree stand, shrubs, cut limbs, rocks, place for protection from natural elements, and combinations thereof.

"Descenting material generators" include generators that produce a material as a gas, a fine mist, a spray with solids, or some combination thereof that is capable of descenting human scents; the materials including, but not limited to, oxidants, ozone, hydroxyl radicals, hydroperoxides, and other known descenting materials; with or without an operating integrated fan. A "mist" produced by an ozonator or descenting material generator is a mist of descenting material and a liquid, e.g. water or organic-solvent material (e.g. alcohols like methanol or ethanol or isopropanol or glycol ether, e.g. ethylene glycol methyl ether and ethylene glycol dimethylether) that is capable of solubilizing descenting material. Ozone generators of all sizes, weights, power sources and types are widely available from sources such as Sharper Image (www.sharperimage.com), Biozone Scientific (www.biozonescientific.com), Ozone Solutions (www.ozoneapplications.com) and Air Zone (www.aaaozone.com). Optionally, the ozone generator contains an additional ion generator source for negative ionization of the air. These type of units are commercially available, e.g. IONIC BREEZE (Trademark) products from Sharper Image. Optionally, the ozone generator is of the type that includes atomized water or hydrogen peroxide to produce highly reactive hydroxyl radicals. Such generators are disclosed, e.g., in Japanese patent references JP11-00948A; JP11-009949A; JP2003001/237A2; JP11-226108A; and JP 11-226106A. Optionally, the ozone generator can include the simultaneous or intermittent generation of other known oxidizing agents, bacteria and odor removing substances such as chlorine, zinc ricinoleate and/or cyclodextrine, e.g. as contained in FEBREEZE (Trademark) fabric softener. For hunting purposes it is preferable that the unit be light weight, portable, and battery and/or solar power operated and/or with a hand crank generator, e.g., when walking to a hunt. When hunting from a stationary location, such as blind or tent, it is preferable to have the same features, but if a portable generator or source of AC electric power is available, then ozone generators having this capability are also preferred. When hunting from a blind or a tent, it is still preferred to use low weight generators since the generator often needs to be transported, e.g., carried from a lodge, cabin or vehicle, e.g. to a watching or hunting location; but generators weighing up to about 8 lbs. and more may also be used. In general, light weight ozone generators produce lower levels of ozone and generate ozone for a shorter period of time, especially when small batteries such as size A, AA, AAA, C, D and 9 volt batteries are used. However, many battery operated portable ozone generators last eight hours and more on one battery charge. The ozone generation source can be of any type including a UV lamp, electrical discharge, or combination of both. Certain portable, battery-operated and solar-operated ozone generators have UV lamps as the ozone generator source due mainly to the lower voltage required for UV lamps. Larger ozone generators capable of operating on AC current can be UV lamp, electrical discharge or a combination of both. Electrical discharge ozone generators can be capable of generating larger amounts of ozone in a smaller size container, but adding blowers, fans and transformers (which is within the scope of the present invention) can result in some generators being heavier than ozone generators having UV lamps. Small, portable battery and solar operated ozone generators are available which have small fans, though many have no fan at all. One advantage of including at least a small fan is that the ozone can be dispersed over a larger area more readily, but it is not necessary that a fan be included in the ozone generator. For ozonating a larger area like a tent, especially when two or more hunters are occupying the tent, an ozone generator having a fan or fan blower is preferred, but not required. If a fan or fan blower is used, a fan can be used which makes minimum noise, especially beyond about a ten foot radius of fan operation so as not to spook an animal, e.g. a deer.

Certain ozone generators are capable of producing 1 mg and up to 5,000 mg/hr of ozone and more. For safety consideration, in certain embodiments of the present invention a person is exposed to a constant concentration of 0.1 ppm ozone or less and, in one aspect, such a concentration over an 8 hour time period or less; but exposures to larger concentrations up to 0.2 ppm ozone and more over short periods of time can be tolerated by most humans. One preferred ozone generator is one which can maintain about 0.1 ppm or less total ambient concentration of ozone over an area of approximately a six foot radius of a human. In certain aspects the present invention provides methods for reducing foreign scent in a space between a human being and an animal, the methods including generating descenting material with a generator, introducing the descenting material into a space or zone between a human being and an animal, the space or zone containing foreign scent, and reducing the foreign scent in the space or zone with the descenting material. In certain embodiments, the descenting material is ozone and the method further includes: exposing the human being to a time-weighted average value of 0.1 ppm ozone in air or less over an area within a radius of six feet of the human being; exposing the human being to a time-weighted value of 0.2 ppm ozone in air or less; or exposing the human being over a time period of eight hours or less to a time-weighted value of 0.1 ppm ozone in air or less. In other aspects the present invention provides methods for reducing foreign scent in a space or zone between a human being and an animal, the methods including producing descenting material with a generator, with direction apparatus, directing said descenting material in a desired direction into the space or zone, the direction apparatus including at least one director in communication with the generator for receiving produced descenting material from the generator and for directing said descenting material into the space or zone, and reducing the foreign scent in the space or zone with the descenting material. In certain embodiments of such methods the descenting material is ozone and the method further includes: exposing the human being to a time-weighted average value of 0.1 ppm ozone in air or less over an area within a radius of about six feet of the human being; exposing the human being to a timeweighted average value of 0.2 ppm ozone in air or less; or exposing the human being over a time period of eight hours or less to an ozone concentration of a time-weighted average value of 0.1 ppm ozone in air or less. For humans that are pursuing an encounter with an animal in a leisure manner, e.g. those hunting and producing only small amounts of odor via sweat and lighter breathing, a small battery generated ozone generator like the BIOZONE Model 50 Personal Air Purifier capable of operating on four C batteries can be used. For persons engaging in an animal-encounter activity, e.g. photography or hunting, for an extended period, e.g. an hour, two hours, three hours, four hours, or more hours, a larger ozone generator such as the BIOZONE SCIENTIFIC TRAVELAIRE (Trademark) generator weighing about 8 oz. or an OMZ-200 (Trademark) generator from Ozone Solutions weighing about 12 oz. and operating only with larger batteries or AC can be used. For those engaging in mostly stationary activity, e.g. hunting outdoors or in a tent or blind, then an ozone generator such as the OZONE SOLUTIONS Model MZ-450 can be used which is capable of deodorizing 2,000 sq. ft. with it's 450 mg/hr ozone generation and 61 cfm (cubic feet per minute) fan, or a 6 lb. OZONE SOLUTIONS OMZ-3400 having a 3,400 mg ozone output and 34 cfm fan can be used. The MZ-450 and OMZ-3400 are primarily suited for 110V operation, but can be operated with larger batteries e.g. batteries currently weighing about 4 lbs. and capable of operating for four or more hours on a single battery charge. As battery technology improves, it may be possible to operate high ozone concentration generators with batteries that weigh much less.

The use of ozone can quickly reduce or eliminate odors (including human odors), volatiles and contaminates (all collectively referred to as "foreign scents") on a person or his or her clothing and equipment and in the space between the person and an animal that may be alerting wildlife to the presence of a human. The ozone is cleanly reduced to oxygen. The many uses of ozone that are known to kill bacteria, eliminate smoke and react with alcohols, esters, saturated organics, acyclics, aromatic, heterocyclics and more to purify the air for healthier human consumption are used in certain methods according to this invention not to purify the air for human breathing, e.g. for a hunter normally in a very clean outdoor environment, but to react with odors emitted by humans so that these volatiles are not detected by an animal, e.g. a deer. Since ozone has a half-life of 20 minutes or more, airborne unreacted ozone still continues to clean bacteria, odors or clothing. In addition, any gear that has odor emanating from the gear is also cleaned. Without being bound by any theory, it is believed that in one aspect, ozone in the air kills bacteria in certain body areas, including, but not limited to, in the underarm and groin areas that is responsible for producing many of the odor-causing volatiles emitted by humans; and in another aspect, any volatile odors that are produced and emitted directly by humans via the skin are oxidized by the ozone into compounds that are much less volatile and therefore far less detectable to animals, e.g. deer. In another aspect, it is believed that any volatile odors that are produced and emitted directly by humans via the feet and escape through the shoe or socks are oxidized by the ozone into compounds that are much less volatile and therefore far less detectable to deer. In yet another aspect, it is believed that the more powerful (but much shorter life-time) hydroxyl and/or hydroperoxide radical oxidants that are produced by ozone reacting with ultraviolet rays of the sun and/or the UV lamp of an ozone generator and/or moisture in the air contribute to odor elimination.

In yet another aspect, it is believed that any pheromone or combinations of pheromones (which contain a wide variety of alcohol, ester, and saturated organic functionality) that are produced and emitted by humans at levels far to small to be detectable by humans but not by animals, e.g. deer, are oxidized by the ozone into compounds that are much less volatile and therefore far less detectable to animals, e.g. deer. In yet another aspect, it is believed that odorants in breath such as aldehydes, alcohols and acids are oxidized by the ozone into compounds that are much less volatile and therefore far less detectable to animals, e.g. deer. In yet another aspect, it is believed that it is possible that oxidized volatiles, even if they are still somewhat volatile and detected by animals, e.g. deer, are changed enough in composition that the animals, e.g. deer, no longer detects the oxidized volatiles as human.

In yet another aspect, it is believed that it is possible that higher levels of ozone in the environment around animals, e.g. deer, overpowers any human volatile such that the animals, e.g. deer, perceive the higher concentration of ozone as the result of commonly-occurring and natural lightning that may be miles away from the animals, e.g. deer.

Prior to descenting of clothes, use of special soaps, shampoos and carbon and/or metal containing clothing, or combinations of these is optional, but not necessary, when using ozone for animal encounters, e.g. hunting. There is no limitation to the number of ozone generators used except for taking the precaution of not allowing a person to come into contact with an unsafe amount of ozone that affects human health. For cost and convenience, one ozone generator located on or near a person is sufficient. Multiple generators located on a person, near a person as the person is walking, inside a blind, outside of a blind, and combinations thereof, may result in an especially enjoyable activity, e.g. a hunt.

The ozone generator or generators are, in one aspect, located approximately 1-2 feet above a person's head. It is within the scope of the present invention to locate an ozone generator at a person's feet or near any part of a person's body. Heights greater than about five feet above the head may be used, but it is possible that too much dispersion of the ozone results in less ozone contacting and then eliminating odors emanating from a person to effectively prevent an animal from detecting a human or to attract an animal. In certain aspects, an ozone generator is placed in a position that is substantially upwind of a person, e.g. a hunter, and slightly elevated above the person's head such that the ozone effectively contacts and then reduces or eliminates odors emanating from the person.

Referring now to FIG. 1, in one embodiment 10 of systems and methods according to the present invention an ozone generator G is located on a person P in a blind B, e.g. a hunter, especially when the person is walking to an activity site, e.g. a hunt site or engaged in an activity, e.g. hunting. The person P is wearing clothes C which may be any typical clothing or which may be any clothing disclosed herein according to the present invention.

Optionally the blind B has an interior ozone generator N and/or an exterior ozone generator R. Optionally an ozone generator T is placed outside the blind B. The person P may be outside the blind B. The blind may be a fabricated structure or a home-made blind on the ground or in a tree, e.g. made of conveniently located brush and foliage. The blind may be a unit such as an enclosure, hut, or a tent that is brought to the sight or permanently located at the site.

According to certain aspects of the present invention, there is provided a method for the de-scenting of clothing used by sportsmen by the use of an oxidizing gas, namely, ozone or by ionization with UV light to produce hydroxyl and hydroperoxide ions. More particularly, clothing is treated with ozone or the hydroxyl and hydroperoxide ions either at home or in the field by the application of a small amount of ozone or the hydroxyl and hydroperoxide ions in order to remove the human scent or any other foreign scent. Also, the clothing of fishermen can be treated with the oxidizing gas while in the field to remove the odor of fish.

According to one embodiment of the invention, the human scent can be eliminated from clothing by applying a low volume stream of an oxidizing gas comprising ozone or hydroxyl and hydroperoxide ions directly on the hunter while he is wearing a hunting outfit. The gaseous stream is applied by an ozone generator which is hand held or a catalytic ionizer containing UV light and easily transported by the hunter. The gaseous stream can be applied directly to the clothing being worn by the hunter in an open atmosphere so as to be quickly diluted after it is passed over the clothing. Moreover, the gun or rifle or any other equipment, i.e. ammunition, arrows, scope, finders etc., of the hunter or sportsmen can be similarly treated to remove the gun or rifle or equipment odor.

In accordance with another embodiment of the invention, the human scent of a military person desiring to escape detection by other humans or scent animals (e.g. dogs) is reduced or eliminated enough to avoid detection. More particularly, there is provided a method for reducing or eliminating human or any other foreign scent from clothing, e.g. clothing and equipment used by military persons desiring to evade capture—through the use of ozone or hydroxyl and hydroperoxide ions produced by ionization in a manner that would not cause irritation or injury to the user or equipment.

In accordance with another embodiment of the invention, the clothing of the hunter can be treated before or after the hunt by placing the clothing in a container i.e. a sack, bag or box while passing the oxidizing gas into the container in order to remove any human or other scent foreign to that environment.

Another embodiment of the invention is that the generator is carried with a hunter or hung upwind of the body so it descents the human scent traveling downwind. In another embodiment of the invention, the generator is carried or placed with or near a hunter with little or no regard to wind direction, allowing for a full 360 degree hunt.

Also, some certain clothing is not cleaned after every use by the hunter or sportsmen such as gloves, hats, jackets, boots, and need to be deodorized and decontaminated before next use.

According to a further embodiment of the invention, the odor of fish can be eliminated from a fisherman's clothing, body or equipment by the direct application of a stream of ozone gas or hydroxyl and hydroperoxide ions to the site of the fish odor. Additionally, a fisherman's hands can be deodorized with ozone so as to remove the fish odor without causing irritation.

Each of the methods can be practiced in the open in the field of sports activity utilizing a low volume gas generator. The clothing is not decolorized as in applications involved in high volumes of ozone as found in the garment industry where ozone is used to both de-size and/or decolorize denim garments. The oxidizing gas may be used alone or diluted with air as when packaged in a compressed gas form. Ozone which is produced by generators in amounts up to 8000 mg/hr or more can be compressed or diluted with an inert gas and compressed into small containers.

It is understood that the term "sportsmen" is meant to include those individuals who may hunt with a camera or who merely enter an environment to observe animals in their habitat.

Additionally, the term "fishermen" includes those individuals who handle the fish caught by others.

Hydroxyl and hydroperoxides are produced in a process known as "Radiant Catalytic Ionization" which utilizes ultra violet light which activates a photocatalytic target.

Small ozone generators such as those producing 1 to 25 lbs. of ozone per day can be utilized. Also the ozone can be applied from compressed ozone-filled containers similar to compressed air.

Low volume ozone generators which generate up to 65 mg/hr of ozone and are portable as well as high volume ozone generators are currently sold by EcoQuest International of Greeneville, Tenn. which also sells the generators of hydroxyl and hydroperoxide ions.

It will be appreciated by persons skilled in the art that numerous variations and/or modifications may be made to the invention without departing from the spirit or scope of the invention as broadly claimed.

The present invention discloses methods of reducing or of eliminating any scent that is foreign to the environment from the clothing, equipment and body of sportsmen, by generating a volume of ozone gas or a gaseous stream of hydroxyl and hydroperoxide ions produced by catalytic ionization and passing the gas over the clothing, body, or equipment. Such a method may include any of the following: wherein said scent is human scent or any other scent that is not natural to the environment; passing said gas over a gun or rifle of said sportsman; wherein said sportsman is a hunter; wherein said scent is fish odor; wherein said gas is generated by a hunter at the field of the hunt; wherein the clothing is treated with said gas while being worn by the sportsmen; wherein said clothing and equipment is treated with said gas when in a container; wherein said gas is ozone; wherein said gaseous stream is produced by catalytic ionization; and/or wherein said gas is compressed and delivered from a container. The present invention discloses a method for removing the human scent and any other scent that is not advantageous to the environment you are in from clothing and equipment used by sportsmen by the use of gaseous ozone or hydroxyl and hydroperoxide ions. The gas is applied directly or indirectly to the clothing, equipment and body while the hunter is in the field and/or prior to or after the hunt. The method can also be used by fishermen to eliminate fish odor. The method can include delivering a gas in compressed/generated form from a generator that is a container.

The following Examples further illustrate the invention, but are not intended to be limiting thereof. In these examples ozone concentration monitoring was done with an OS-4HIGH RANGE (Trademark) ozone sensor from Eco Sensors, Inc. of Santa Fe, N. Mex.

EXAMPLES

Example I shows how ozone reduces underarm odor from humans.
Examples II-X show how ozone reduces odors associated with human antiperspirants and perfumes.
Examples XI-XII show how ozone can eliminate odors in a tent or blind.
Examples XIII-XXVII show how ozone can eliminate odors from cloth, rags, and clothes placed in a container (e.g. garment bag, luggage, or cooler) and treated with ozone.
Example XXVII shows how ozone treatment results in an improved hunting experience.

Example I

Ozone from a DC PRO 450 HO (Trademark) generator was directed to the underarm of a human for a period of 30 seconds. The odor before treating with ozone was a 10 on a personal odor scale ("POS") scale in which bad odor is at worst a "10" and reduced odor is less than 10, and after treatment the odor was a less than 1 on the POS scale.

Example II

Stick deodorant, Right Guard EXTREME (Trademark) deodorant, was wiped onto the back of a human hand. The odor from the deodorant before treating with ozone was a 10. After 5 minutes treatment with ozone using the DC PRO 450 HO ozonator within 12 inches of the hand, the smell was very faint (<1 on the POS scale).

Example III

Male cologne, Calvin Klein's OBSESSION FOR MEN (TM) cologne, was sprayed twice on the back of a human hand. The odor before treating with ozone was a 10. After four minutes treatment with ozone using the DC PRO 450 HO (Trademark) ozonator within 12 inches of the hand the smell was very faint (<1 on the POS scale).

Example IV

Example III was repeated but the cologne was sprayed only once on the back of a human hand. The odor before treating with ozone was a 10. After 5 minutes treatment with ozone using the DC PRO 450 HO (Trademark) ozonator, the smell was very faint (<1 on the POS scale).

Example V

Human hands had smoke and cigarette smell thereon from campfire and lighting of cigarette. The odor before treating with ozone was a 10. After 2 minutes treatment with ozone using the DC PRO 450 HO (Trademark) ozonator the smell was very faint (<1 on the POS scale).

Example VI

A human rubbed both hands liberally with a sliced onion and placed hands in front of a DC PRO 450 HO (Trademark) ozonator. The odor before treating with ozone was a 10. After two minutes treatment with ozone, the smell was gone (0 odor).

Example VII

A human rubbed fresh crushed garlic on both hands and placed one of the hands in front of DC PRO 450 HO (Trademark) ozonator (within 12 inches). The odor before treating with ozone was a 10. After two minutes and 20 seconds treatment with ozone the smell was faint (less than 1 on the POS scale). After six minutes the smell negligible, and after eight minutes the smell was gone (0 odor). By comparison, the hand not treated with ozone remained a 10 (on the POS scale) after eight minutes.

Example VIII

A human rubbed MAGIC BAIT (Trademark) bait (chicken liver and chicken blood combination on both hands and placed one of the hands in front of the DC PRO 450 HO (Trademark) ozonator (within 12 inches). The odor before treating with ozone was a 10 (on the POS scale). After ten minutes the hand treated with ozone had about a 2 odor (on the POS scale). By comparison, the hand not treated with ozone remained a 10 (on the POS scale) after ten minutes.

Example IX

A human rubbed an ORKA BAY WILD COD (Trademark) fillet on both hands and placed one of the hands in front of DC PRO 450 HO (Trademark) ozonator (within 12 inches). The odor before treating with ozone was a 10. After seven minutes the hand treated with ozone had a 1 odor (on the POS scale). By comparison, the hand not treated with ozone remained a 10 (on the POS scale) after ten minutes.

Example X

A back of a human hand was sprayed with two sprays of Ralph Lauren ROMANCE (Trademark) perfume. The odor before treating with ozone was a 10 (on the POS scale). After five minutes treatment with ozone using the ozonator the smell was faint (2 odor on the POS scale).

Example XI

Placed Glade CINNAMON APPLE PLUG-INS SCENTS (Trademark) in two tents, each with a volume of about 125 cubic feet. After 2 hours, the smell in both tents was a 10 (on the POS scale). In one tent a BIOZONE DC PRO 3400 (Trademark) ozonator was turned on. At the time intervals stated below, the odor level (on the POS scale) in the tents was as follows:
(Ta=Tent without ozone; Tb=Tent with ozone)
10 Minutes
Ta—10
Tb—6
20 Minutes
Ta—10
Tb—5
30 Minutes
Ta—10
Tb—4
45 Minutes
Ta—10
Tb—0

Example XII

Placed Air Wick TROPICAL MIST PLUG INS (Trademark) on plug-in control set at a setting of MAX ODOR in a tent with a PRO 3400 (Trademark) ozonator with an Eco Sensors sensor; and in a second "control" tent with no ozonator, placed an Air Wick TROPICAL MIST PLUG INS (Trademark) on plug-in control set at a setting of MAX ODOR with all tent doors and flaps closed. After 30 minutes both tents had 10 odor (on the POS scale). Then the ozonator with the plug-ins at a control setting of MAX ODOR, was turned on and ozone levels in the tent with the ozonator rose as follows (with odor levels in both tents, on POS scale, as indicated):
0 minutes=0.00 ppm
1 minute=0.26 ppm
2 minutes=0.50 ppm
3 minutes=0.71 ppm
4 minutes=0.87 ppm
5 minutes=1.02 ppm (odor in ozonated tent, 4; in control tent, 10)
15 minutes=2.43 ppm (odor in ozonated tent, 3; in control tent, 10)
21 minutes=2.35 ppm (odor in ozonated tent, 3-4; in control tent, 10)
At 21 minutes, turned output of both plug-ins to a 0.5 control setting.
31 minutes=2.42 ppm
36 minutes=2.34 ppm (odor in ozonated tent, 4; control tent, 10)
41 minutes (unplugged both plug-ins and removed from tents)
56 minutes=2.97 ppm (odor in ozonated tent, 1; control tent, 10)
71 minutes (set both plug-ins on a "low" control setting in each tent
81 minutes=2.81 ppm (odor in ozonated tent, 1; control tent, 10)

Example XIII

An ENVIROSORB (Trademark) cellulose solvent pillow (available from Lab Safety Supply, Inc.) was saturated with butyl mercaptan vapors by placing an open bottle of butyl mercaptan in a closed metal paint can containing the pillow. The vapor-saturated pillow was then placed in a DILLARD'S (Trademark) garment bag along with a DC PRO 450 HO (Trademark) ozonator. The odor before treating with ozone was a 10 (on the POS Scale). After 20 minutes with the ozonator on in the bag, treated imbiber had a smell of 1 on the POS scale.

Example XIV

Approximately 0.5 ml of butylmercaptan was added to 10 ml denatured alcohol in a SEP (Trademark) commercial sprayer. Five sprays of the mixture were sprayed on a cotton t-shirt. The shirt was placed in a garment bag along with a DC PRO 450 HO (Trademark) ozonator. The odor before treating with ozone was a 10 (on the POS Scale). After 20 minutes treating with ozone in the bag, the treated shirt had a smell of 2 on the POS scale and a control shirt (no treatment) had a smell of 10 on the POS scale.

Example XV

Ralph Lauren ROMANCE (Trademark) fragrance was sprayed twice on a cotton shirt and placed in the garment bag of Example XIII along with a DC PRO 450 HO (Trademark) ozonator. The control shirt was sprayed two times with the fragrance and placed in open air. The odor on both shirts before treating with ozone was a 10 (on the POS scale). After 10 minutes of ozone treatment in the bag, the treated shirt had a smell of 0 and the control shirt had a smell of 10.

Example XVI

One spray of LEMON FRESH PINESOL (Trademark) liquid was sprayed on each of two cloths. One cloth was placed in the garment bag of Example XIII with a DC PRO 450 HO (Trademark) ozonator, and the other cloth (control) was placed outdoors. The odor on both cloths before treating with ozone was a 10 (on the POS scale). After 6 minutes of ozone treatment in the bag the treated cloth had a smell of 0 on the POS scale and the control cloth had a smell of 2 on the POS scale.

Example XVII

Smoke from a small fire of had and small twigs was allowed to permeated 2 cloths. One cloth was placed in the garment bag of Example XIII with a DC PRO 450 HO (Trademark) ozonator and the other cloth (control) was placed outdoors. The odor on both cloths before treating with ozone was a 10 (on the POS scale). After 5 minutes of treating with ozone, the treated cloth had a small of 0 on the POS scale and the control cloth had a smell of 6 on the POS scale.

Example XVIII

Smoke from a lit cigarette was blown into two cloths. One cloth was placed in the garment bag of Example XIII with DC PRO 450 HO (Trademark) ozonator, and the other cloth (control) was placed outdoors. The odor on both cloths before treating with ozone was a 10 (on the POS scale). After 6 minutes of treating with ozone in the bag, the treated cloth had a 0 smell on the POS scale and the control cloth had a smell of 6 on the POS scale.

Example XIX

Ralph Lauren ROMANCE (Trademark) fragrance was sprayed twice on the outside of a SCENT-LOK SAVANNAH EXT (Trademark) jacket. At time=0, the smell of the sprayed jacket was a 10 on the POS scale. After 5 minutes in the open air the smell was still an 8 on the POS scale. The jacket was then placed in the garment bag of Example XIII with a PRO 3400 (Trademark) ozonator. After treating the jacket for 10 minutes in the bag with ozone the smell was a 2 on the POS scale. After 15 minutes of ozone treatment in the bag the odor of the jacket was a 1 on the POS Scale. After 20 minutes of such treatment the odor was gone.

Example XX

The inside lining of a jacket as in Example XIX was sprayed with the ROMANCE (Trademark) fragrance and placed inside the bag of Example XIII with a PRO 3400 (Trademark) ozonator. At time=0, the smell was a 10 on the POS scale. After treating the jacket for 5 minutes in the bag with ozone the smell was a 3 on the POS scale. After 10 minutes of ozone treatment in the bag the odor of the jacket was a 1-2 on the POS scale. After treating the jacket for 15 minutes in the bag with ozone the smell was a 0-1 on the POS scale. After 20 minutes the odor was gone.

Example XXI

ROMANCE (Trademark) fragrance was sprayed onto two cloth rags with four sprays of the fragrance each. One cloth was placed in a bag as in Example XIII with a PRO 3400 (Trademark) ozonator and the other cloth (control) was placed outside. At time=0, the smell on both rags was a 10 on the POS scale. After 5 minutes the ozone-treated rag was a 0 on the POS scale and the outside cloth was a 2 on the POS scale.

Example XXII

Two rags were each sprayed with two sprays of Calvin Klein OBSESSION FOR MEN (Trademark) cologne plus four sprays of the Ralph Lauren ROMANCE (Trademark) fragrance. One rag was placed in a bag as in Example XIII with a PRO 3400 (Trademark) ozonator and the other rag was placed outside. At time=0, the smell on both rags was a 10 on the POS scale. After 5 minutes of treatment, the ozone cloth in the bag had a smell of 0 on the POS scale and the cloth outside had a smell of 10 on the POS scale.

Example XXIII

The OBSESSION (Trademark) cologne was sprayed (2 sprays) on two SCENT-LOK SAVANNAH EXT coats. One coat was placed in a bag as in Example XIII with a PRO 3400 (Trademark) ozonator. The other coat (control) was placed in the open air. The results are below:
TIME
CONTROL COAT SMELL
COAT TREATED WITH OZONE
(SMELLS ON POS SCALE)
0 Minutes
 10
 10
5 Minutes
10
7
7 Minutes
10
4
13 Minutes
8
3
18 Minutes
7
2
(e.g. at 7 minutes the control coat had a smell of 10 and the treated coat had a smell of 4)

Example XXIV

The OBSESSION (Trademark) fragrance was sprayed (2 sprays) each onto one sweat shirt, one camouflage t-shirt (short sleeved), one camouflaged long-sleeved t-shirt, one pair of denim jeans, one cotton short pants and one cotton t-shirt. All the clothes were placed in a bag as in Example XIII in no order along with a PRO 3400 (Trademark) ozone generator. The smell at time=0 in the bag was a 10 on the POS scale. After 95 minutes treatment with ozone in the bag, each garment had a less than 1 smell on the POS scale. Ten hours later, all the clothes placed in the bag still had ozone odor on them. At this time all the clothes were placed in an unsealed plastic bag and another 14.5 hours later the clothes still had ozone odor on them.

Example XXV

One spray of COON URINE (Trademark) Hunter's Masking Scent was sprayed onto a t-shirt. The t-shirt was placed into a bag as in Example XIII along with a BORA IV LIVING AIR (Trademark) ozonator (fan on max). The results are shown below for the indicated number of minutes of treatment with ozone in the bag:
0 minutes=10 odor (odor of shirt on POS scale)
5 minutes=6 odor
10 minutes=2 odor
15 minutes=1 odor Example XXVI One spray of the OBSESSION (Trademark) cologne was sprayed onto a POLAR TEC (Trademark) fleece jacket and placed into a 150 quart cooler fitted with a clothes rod and hanger. The fleece jacket was placed on the hanger and a PRO 3400 (Trademark) ozone generator was placed into the cooler. The smell at time=0.0 in the cooler was a 10 on the POS scale. After 15 minutes treatment with ozone, the garment had about a 1 smell on the POS scale.

Example XXVII

On spray of the OBSESSION (Trademark) cologne was sprayed on a green long-sleeved shirt (100% cotton knit) and placed in the cooler as described in Example XXVI along with a PRO 3400 (Trademark) generator. A small fan was placed in the bottom of the cooler and turned on max with the fan facing up. The smell at time=0 in the cooler was a 10 on the POS scale. After 15 minutes of treatment with ozone in the cooler, the shirt had about a 1 smell on the POS scale. Then the shirt was re-placed in the cooler and treated with ozone for an additional 30 minutes. This resulted in several red streaks on the shirt due to the ozone contacting and remaining on the shirt. The shirt was then removed from the cooler and placed on a table open to the ambient air. About eleven hours later, the shirt still had an ozone smell and almost all the red streaking had disappeared. Another 12 hours later minimal ozone smell was noticeable and all red streaking had disappeared.

Example XXVIII

A sweaty t-shirt that a human jogged in for 3.5 miles over 35 minutes was placed on a hanger in the cooler of Example XXVI along with a PRO 3400 (Trademark) ozone generator and a small fan in the cooler was turned on high. The smell at time=0 in the cooler was a 10 on the POS scale. After 20 minutes treatment with ozone in the cooler, the garment had about a 2 smell on the POS scale.

Example XXIX

A hunter placed himself in a cedar bush located in the Fort Peck Wilderness Area in Montana. A Biozone 50 (Trademark) battery-operated ozonator was placed on a backpack located between the hunter's legs and turned on. An elk was observed approaching within 8 yards of the hunter about 45 minutes after the ozonator was turned. The elk passed downwind and through the hunter's scent line without detecting the hunter.

Example XXX

A hunter placed himself in a home-made blind of native brush in South Texas along with an OMZ-200 (Trademark) battery operated ozonator hung from the blind and located about 10 inches behind and above his head. The hunter did not use any SCENT-LOK (Trademark) clothing, masks or scents prior to or during the hunt, but was camouflaged using Cabela's lightweight ghillie pants, jacket and facemask. Deer corn was placed at the perimeter of the blind going out to about 30 feet from the blind. Within 10 minutes of turning on the ozonator to Max Setting, up to 6 white tail deer at a time and several birds (cardinals and finch) were observed feeding within 10 yards downwind of the hunter in a 3 hour time span. One young buck was observed within 5 feet downwind of the blind where the hunter was laying. None of the deer, cardinals or finch appeared to have scented the hunter.

Optionally, a feeder FR is provided to attract an animal (e.g., but not limited to, a grain feeder for attracting a deer or a bird feeder for attracting a bird). Any known feeder may be used, including but not limited to, an automatic powered timed feeder. An ozone generator X connected to or adjacent the feeder FR produces ozone to descent the feeder, the feed, and/or the area around the feeder.

In all the Examples I-XXX the ozonator or generator included a fan as part thereof and this fan was operating when the ozonator or generator was turned on.

Figure 2:
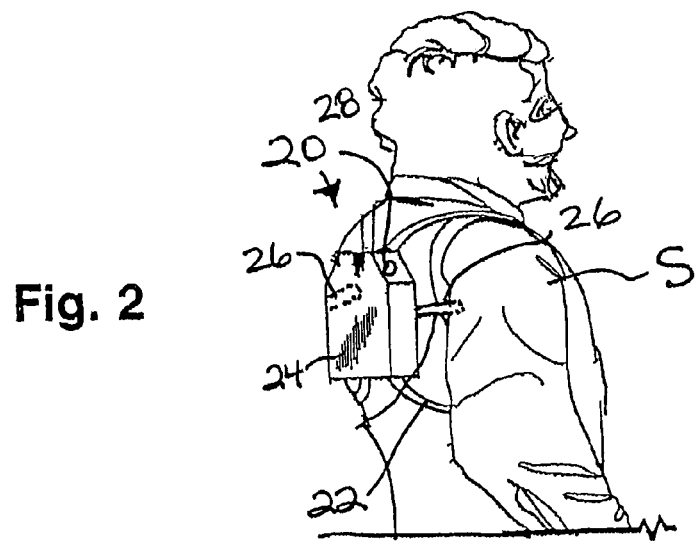
FIG. 2 is a perspective view of a system according to the present invention.

FIG. 2 shows a person S with an over-shoulder removable harness 22 of a system 20 according to the present invention. An ozone generator 24 is connected to the harness 22. Optionally produced ozone is directed to the person's underarms by tubes 26. Optionally, produced ozone is expelled from the ozone 24 via a port 28.

Figure 3:
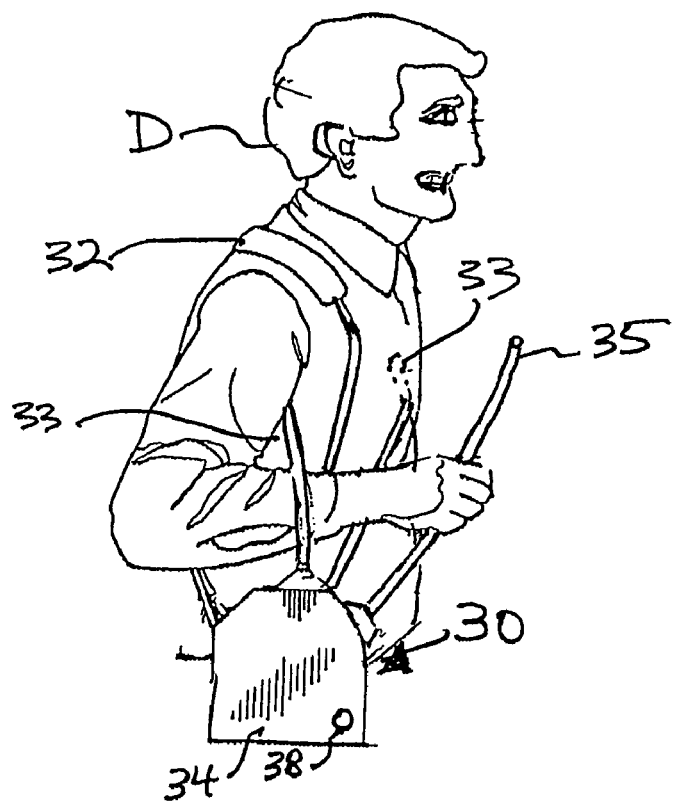
FIG. 3 is a perspective view of a system according to the present invention.

FIG. 3 shows a person D with a system 30 according to the present invention. A shoulder strap 32 supports an ozone generator 34. Optionally produced ozone is expelled through a port 38. Optionally tubes 33 direct produced ozone to the person's underarms. Optionally the system 30 includes a free tube 35 which may be of any desired length and which is movable and/or flexible for directing ozone to any body part and/or toward any item or area.

Figure 4:
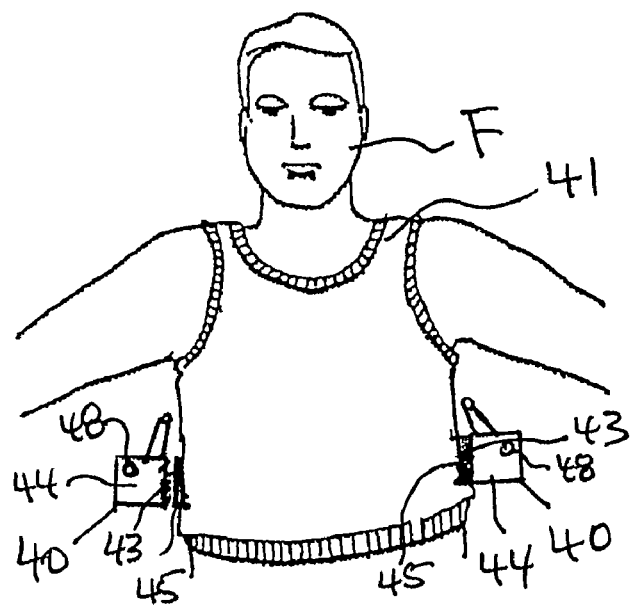
FIG. 4 is a front view of a system according to the present invention.

FIG. 4 shows two systems 40 according to the present invention used by a person F. Each system 40 has an ozone generator 44 with a nozzle 46 for directing produced ozone in a desired direction at a desired body part. Each system 40 has thereon an amount of releasably-cooperating hook-and-loop fastener material 43. A corresponding amount 45 of this material is on a shirt 41 of the person F; thus, the ozone generators 44 are releasably connected to the shirt 41. Optionally, such a connection can be provided for any ozone generator disclosed herein for connection to any piece of clothing, footwear, blind, or other item. Optionally each ozone generator 44 has a produced-ozone exit port 48.

Figure 5:
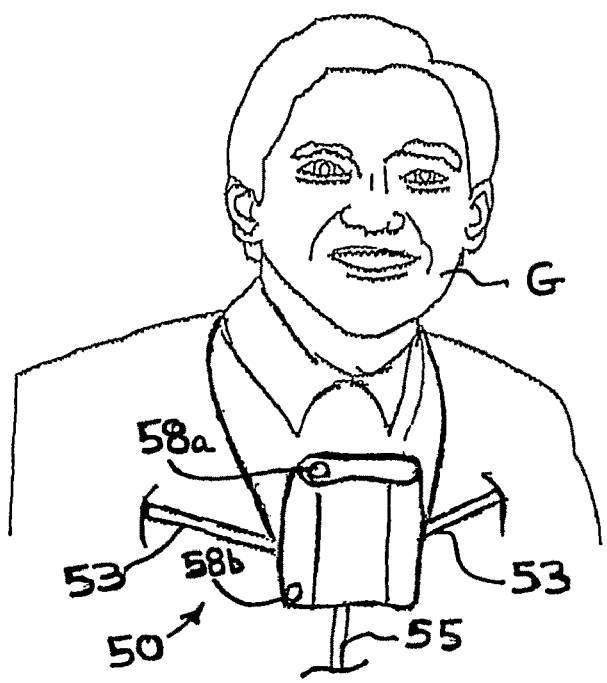
FIG. 5 is a front view of a system according to the present invention.

FIG. 5 shows a person G with a system 50 according to the present invention with an ozone generator 54 worn or a string or cord 51 around the person's neck. Optionally, the system has two tubes 53, one directed to each of the person's underarms. Optionally the system 50 has a tube 55 directed to a body area beneath the person's chest (e.g. but not limited to, to the groin area). Optionally, the ozone generator 54 has a produced-ozone exit port 58a and/or a produced-ozone exit port 58b.

Figure 6:
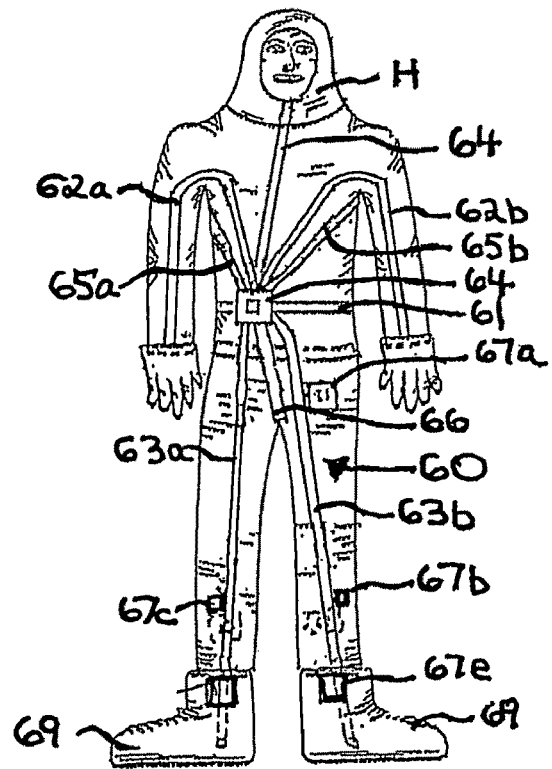
FIG. 6 is a front view of a system according to the present invention.

FIG. 6 shows a person H with a system 60 according to the present invention having an ozone generator 64 worn around the waist on a belt 61. It is within the scope of the present invention for the belt to be around any body part or area (e.g. but not limited to, head, arm, leg, chest, foot). Tubes 62a, 62b, 63a, 63b, 64, 65a, 65b, and 66 extend to various body parts or areas to convey ozone to those parts or areas. Optionally, an ozone generator or generators 67a, 67b, 67c, 67d, and/or 67e may be used with or instead of the ozone generator 64. The tubes 63a, 63b can, as shown extend down into boots 69 or they can be terminated above the boots 69.

FIG. 7 shows a system 80 according to the present invention with an ice chest or cooler 71 with an openable lid 71a and body 71b with an interior space 71c. Shown schematically within the interior space 71c is an ozone generator 72, an optional fan 73, a piece of cloth 74 and an item 75 (shown schematically, may be any thing that will fit within the cooler, including, but not limited to, any item or thing disclosed herein which can be descented with ozone). With the lid 71a closed or open, the ozone generator is turned on to produce ozone to descent the cloth 74 and/or the item 75. When the optional fan 73 is present and turned on, it provides air to circulate the ozone. It is within the scope of the present invention for the ozone generator 72 and the fan 73 to be powered via an electrical power source (not shown) using a typical electrical power cord (not shown); or, as shown, the ozone generator 72 and the fan 73 are battery-operated. Optionally, or in addition to the fan 73, a fan 73a may be used outside the cooler 71 with the lid 71a open.

FIG. 8 shows a system 80 according to the present invention with a flexible bag 81 with an openable zipper 81a and body 81b with an interior space 81c. Shown schematically within the interior space 81c is an ozone generator 82, an optional fan 83, a piece of cloth 84 and items 85, 86, 87 (shown schematically, may be any thing that will fit within the cooler, including, but not limited to, any item or thing disclosed herein which can be descented with ozone). With the zipper 81a closed or open, the ozone generator is turned on to produce ozone to descent the cloth 84 and/or the item 85. When the optional fan 83 is present and turned on, it provides air to circulate the ozone. It is within the scope of the present invention for the ozone generator 72 and the fan 73 to be powered via an electrical power source (not shown) using a typical electrical power cord (not shown); or, as shown, the ozone generator 72 and the fan 73 are battery-operated. Optionally, or in addition to the fan 83, a fan 83a may be used outside the flexible bag 81, with the zipper 81a open or closed.

Figure 9A:
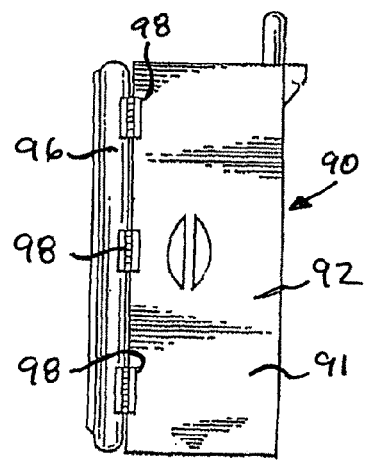
FIG. 9A is a side view of the system according to the present invention.
Figure 9B:
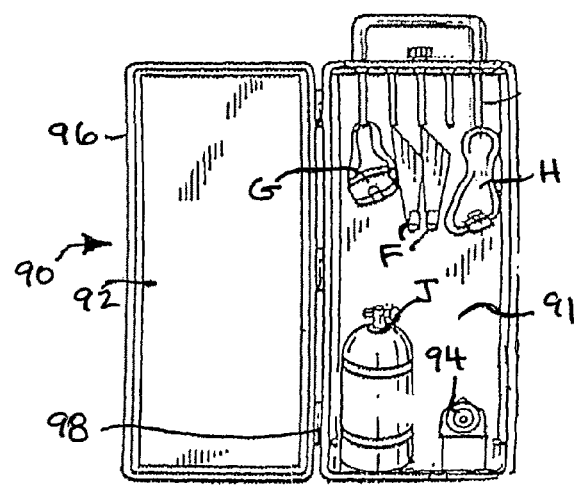
FIG. 9B is an open front view of the system of FIG. 9A.

FIGS. 9A and 9B show a system 90 according to the present invention which includes a portable container 92 with a hinged lid 96 connected with hinges 98 to a main body 91. As shown in FIG. 9B (with the lid 96 open) the interior of the container can contain a plurality of items, e.g., but not limited to, diving gear F, G, H, J. An ozone generator 94 is placed within the container 92 and, with the lid 96 open or closed, the ozone generator 94 produces ozone to descent the items F-J. It is within the scope of the present invention for the ozone generator 72 and the fan 73 to be powered via an electrical power source (not shown) using a typical electrical power cord (not shown); or, as shown, the ozone generator 72 and the fan 73 are battery-operated.

Figure 10A:
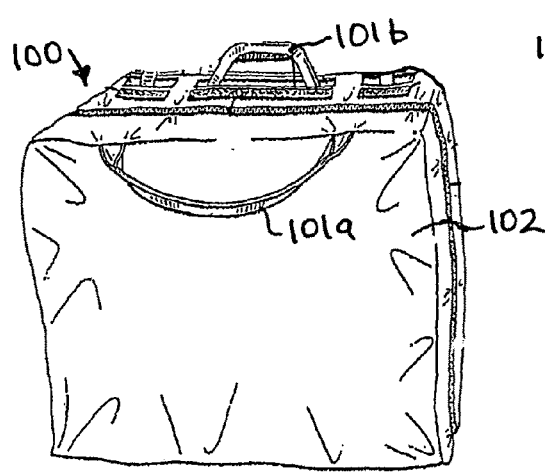
FIG. 10A is a front perspective view of a system according to the present invention.
Figure 10B:
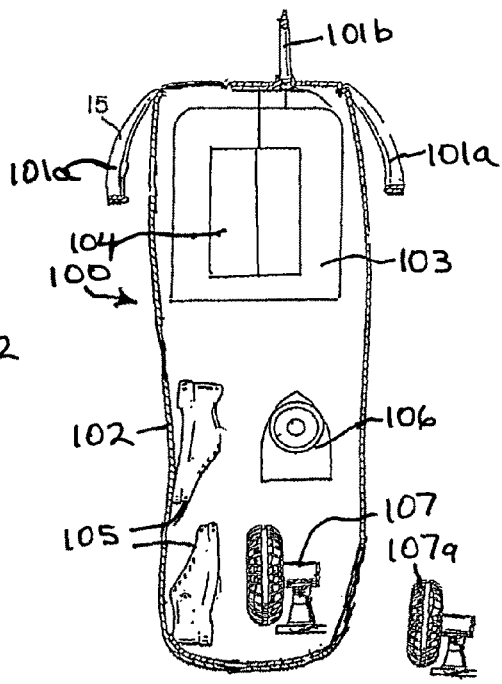
FIG. 10B is an unfolded cross-section view of the system of FIG. 10A.

FIGS. 10A and 10B show a system 100 according to the present invention which includes a garment bag 102 with handles 101a and 101b and an interior space 101c. The garment bag 102 may contain any thing or item that will fit therein. As shown schematically in FIG. 10B, the garment bag 102 contains items of clothing 103, 104 hung therein and shoes 105. An ozone generator 106 is placed within the garment bag 102 to produce ozone to descent the items therein. Optionally a fan 107 is also used within the garment bag 102. It is within the scope of the present invention for the ozone generator 72 and the fan 73 to be powered via an electrical power source (not shown) using a typical electrical power cord (not shown); or, as shown, the ozone generator 72 and the fan 73 are battery-operated. Optionally, or in addition to the fan 107, a fan 107a may be used outside the bag 102 with the bag 102 open or closed.

It is to be understood for any embodiment disclosed herein that mentions an "ozone generator" that a descenting material generator may be used that produces ozone and/or any, each of, and/or all descenting materials referred to herein and their equivalents, with or without an integrated fan that is operating. In the systems of FIG. 2-FIG. 10A any suitable ozonator, ozone generator, or descenting material generator may be used, with or without a fan that is operating.

The present invention, therefore, provides in certain, but not necessarily all embodiments, a method for reducing foreign scent in a space between a human being and an animal, the method including: generating descenting material with a generator, introducing the descenting material into a space between a human being and an animal, the space containing foreign scent, and reducing the foreign scent in the space with the descenting material. Such a method may include one or some, in any possible combination, of the following: the foreign scent including human odor; exposing the human being to about 0.1 ppm ozone, or less, over an area, e.g. within a radius of six feet or less of the human being; exposing the human being to 0.2 ppm ozone, or less; exposing the human being to ozone produced by the generator over a time period, e.g. over a time period of eight hours or less, and 0.1 ppm, or less (all "ppm" ozone levels are a time-weighted average value in air); the descenting material being ozone and the human being has on an item of clothing and the item of clothing receives an amount of ozone produced by the generator, the amount of ozone sufficient so that ozone is retained on the item of clothing and, in one aspect, the item of clothing is colored and the ozone changes the color of at least part of the item of clothing, and the clothing is, e.g., made of knit fabric, cotton fabric, cotton blended fabric, fibrous fabric or fleece; the descenting material being ozone; the descenting material being any of ozone, hydroxy radicals, hydroperoxides, and oxidants; generating the descenting material as a gas; generating the descenting material in a mist; the human being being a hunter and the animal is an animal hunted by the human being; at least one item in the space, the item having an item foreign scent, the method further including descenting the item foreign scent; the foreign scent including human odor, the method further including supporting the generator on the human being; at least one direction apparatus in communication with the generator, the method further including with the at least one direction apparatus, directing descenting material from the generator in a desired direction; the foreign scent including human odor, the method further including supporting the generator on the human being, wherein there is at least one direction apparatus in communication with the generator, the method further including with the at least one direction apparatus, directing descenting material from the generator in a desired direction at a part of the human being; the part of the human being any of an armpit, torso, head, mouth, nostrils, groin, and feet; the at least one direction apparatus being a plurality of direction apparatuses; the foreign scent being in a blind and the descenting material introduced into the blind; the foreign scent being in a tent and the descenting material introduced into the tent; the foreign scent being any of human odor, volatile material, and contaminating material; the fan apparatus assisting in introducing the descenting material into the space; and/or the fan apparatus being spaced apart from the generator or integral therewith.

The present invention, therefore, provides in certain, but not necessarily all embodiments, a method for descenting foreign scent from an item, the method including: placing an item in a container, the item having a foreign scent, the container containing air, the container located outdoors; generating descenting material in the container with a generator; moving air in the container with a fan apparatus; and reducing the foreign scent with the descenting material; and, in certain aspects, such a method wherein: the descenting material being ozone and the human being has on an item of clothing and the item of clothing receives an amount of ozone produced by the generator, the amount of ozone sufficient so that ozone is retained on the item of clothing; the item of clothing being colored and the ozone changes the color of at least part of the item of clothing; and the fan apparatus is spaced apart from the generator or is integral therewith.

The present invention, therefore, provides in certain, but not necessarily all embodiments, a system for descenting human odors on an item, the system including: a container; a descenting material generator in the container; and a fan apparatus in the container for moving air in the container as descenting material is produced by the descenting material generator.

The present invention, therefore, provides in certain, but not necessarily all embodiments, a system for reducing foreign scent in a space between a human being and an animal, the system including a generator for producing descenting material; and at least one direction apparatus (or a plurality of them) in communication with the generator for receiving produced descenting material from the generator and for directing said descenting material in a desired direction to reduce the foreign scent.

The present invention, therefore, provides in certain, but not necessarily all embodiments, a method for reducing foreign scent in a space between a human being and an animal, the method including: producing descenting material with a generator; with direction apparatus, directing said descenting material in a desired direction into the space, the direction apparatus including at least one director in communication with the generator for receiving produced descenting material from the generator and for directing said descenting material into the space; and reducing the foreign scent in the space with the descenting material. Such a method may include one or some, in any possible combination, of the following: the descenting material is ozone and the method further including exposing the human being to about 0.1 ppm ozone, or less, over an area within a radius of about six feet of the human being; the descenting material is ozone and the human being is exposed to a concentration of 0.2 ppm ozone, of less; the descenting material is ozone and the human being over a time period of eight hours or less is exposed to an ozone concentration of only 0.1 ppm or less.

In conclusion, therefore, it is seen that the present invention and the embodiments disclosed herein and those covered by the appended claims are well adapted to carry out the objectives and obtain the ends set forth. Certain changes can be made in the subject matter without departing from the spirit and the scope of this invention. It is realized that changes are possible within the scope of this invention and it is further intended that each element or step recited in any of the following claims is to be understood as referring to the step literally and/or to all equivalent elements or steps. The following claims are intended to cover the invention as broadly as legally possible in whatever form it may be utilized. The invention claimed herein is new and novel in accordance with 35 U.S.C. §102 and satisfies the conditions for patentability in §102. The invention claimed herein is not obvious in accordance with 35 U.S.C. §103 and satisfies the conditions for patentability in §103. This specification and the claims that follow are in accordance with all of the requirements of 35 U.S.C. §112. The inventors may rely on the Doctrine of Equivalents to determine and assess the scope of their invention and of the claims that follow as they may pertain to apparatus not materially departing from, but outside of, the literal scope of the invention as set forth in the following claims. All patents and applications identified herein are incorporated fully herein for all purposes.

What is claimed is:

1. A method for inhibiting sensing of a hunter by a game animal, the method comprising:
   producing ozone with a generator in an unenclosed space wherein the generator, a hunter, and a game animal are located in the unenclosed space, the unenclosed space containing a foreign scent, the foreign scent being foreign to the unenclosed space, the foreign scent comprising human breath, human bodies, scent from clothing, and scent from hunting equipment;
   creating a downwind zone of ozone by the ozone generator in the unenclosed space between the hunter and the game animal;
   passing the foreign scent into the downwind zone, the ozone reducing the foreign scent in the downwind zone thereby inhibiting sensing of the hunter by the game animal.

2. The method of claim 1 wherein the game animal does not sense the hunter when the hunter is a particular distance from the game animal.

3. The method of claim 2 wherein the distance from the game animal is one of 5 feet, 8 yards, and 10 yards.

4. The method of claim 1 wherein the ozone generator is above the hunter.

5. The method of claim 1 wherein the ozone generator is above the hunter a distance of one of 1 to 2 feet or more than 5 feet.

6. The method of claim 1 wherein the generator is located upwind of the hunter and the game animal is located downwind of the hunter.

7. The method of claim 1 wherein the game animal is a big game animal.

8. A method for reducing foreign scent, the method comprising:
   producing with an ozone generator an ozone zone in an unenclosed space downwind of a hunter, the ozone generator, the hunter, and a game animal being positioned in the unenclosed space with the ozone zone being at least partially surrounding the hunter, the unenclosed space containing foreign scent, the foreign scent being foreign to the unenclosed space, the foreign scent comprising human breath, human bodies, scent from clothing, and scent from hunting equipment;
   reducing the foreign scent in the ozone zone thereby increasing the chances of an encounter between the hunter and the game animal.

9. A method for reducing foreign scent from a hunter in an unenclosed space, where the foreign scent is foreign to the unenclosed space and comprises human body odor, clothing odor, and hunting equipment odor, the method comprising:
   introducing ozone in the unenclosed space to create an ozone zone at a downwind location from the hunter, the hunter and a game animal located in the downwind location in the unenclosed space;
   allowing the foreign scent to pass downwind from the hunter into the ozone zone and reduce the foreign scent in the ozone zone with the ozone.

10. The method of claim 9 wherein the hunter wears an item of clothing, the method further comprising:
    directing a gaseous stream of ozone to the item of clothing so that the item of clothing receives an amount of ozone produced by the generator.

11. The method of claim 10 wherein the amount of ozone is sufficient so that ozone is retained on the item of clothing for several hours.

12. The method of claim 10 wherein the item of clothing has a color and the ozone changes the color of at least part of the item of clothing.

13. The method of claim 9 wherein the ozone may be combined with hydroxy radicals, hydroperoxides, or oxidants.

14. The method of claim 9, the method further comprising:
    exposing the hunter in the unenclosed space to an amount of ozone, the amount of ozone having a time-weighted average value of 0.1 ppm ozone in air or less over an area within a radius of about six feet of the hunter.

15. The method of claim 9 wherein the hunter is exposed to an amount of ozone in the unenclosed space, the amount of ozone having a time-weighted value of 0.2 ppm ozone in air or less.

16. The method of claim 9 wherein the hunter over a time period of eight hours or less is exposed in the unenclosed space to an amount of ozone, the amount of ozone having a time-weighted average value of 0.1 ppm ozone in air or less.

17. The method of claim 9 wherein there is at least one item in the unenclosed space, the item having an item foreign scent, the method further comprising descenting the item foreign scent.

18. The method of claim 9 wherein body odor comprises female menstruating odor.

19. The method of claim 9 wherein the method further comprises supporting the generator on the hunter.

20. The method of claim 9 further comprising providing at least one direction apparatus in communication with the generator, the method further comprising directing, with the at least one direction apparatus, ozone from the generator in a desired direction in the unenclosed space toward at least a part of the hunter.

21. The method of claim 20 wherein the part of the hunter is any of an armpit, torso, head, mouth, nostrils, groin, and feet.

22. The method of claim 9 wherein the foreign scent is any of human odor, volatile material, and contaminating material.

23. The method of claim 9 further comprising:
generating the ozone in the unenclosed space as a gas.

24. The method of claim 9 further comprising:
generating the ozone in a mist.

25. The method of claim 20 wherein the at least one direction apparatus is a plurality of direction apparatuses.

26. A method for reducing foreign scent from a hunter, clothing worn by the hunter, and equipment used by the hunter which may be detectable by a game animal, the hunter and the game animal being located in an unenclosed space, the method comprising:
producing descenting material comprising ozone with an ozone generator;
introducing the descenting material into an unenclosed space downwind of the hunter between the hunter and the game animal to create a zone of descenting material;
reducing foreign scent from the hunter, the clothing, and the hunting equipment in the zone of descenting material by the ozone to reduce the foreign scent detectable by the game animal;
directing at least a portion of the descenting material directly onto at least one of the hunter, the clothing, and the equipment to reduce the foreign scent detectable by the game animal.

27. The method of claim 26, further comprising:
exposing the hunter to an amount of ozone in the unenclosed space, the amount of ozone having a time-weighted average value between greater than 0 and 0.1 ppm ozone in air over an area within a radius of about six feet of the hunter.

28. The method of claim 26 wherein the hunter is exposed to an amount of ozone in the unenclosed space, the amount of ozone having a time-weighted average value between greater than 0 and 0.2 ppm ozone in air or less.

29. The method of claim 26 wherein the hunter over a time period of eight hours or less is exposed to an amount of ozone in the unenclosed space, the amount of ozone having a time-weighted average value between greater than 0 and less than or equal to 0.2 ppm ozone in air.

30. The method of claim 26 wherein the amount of descenting material is sufficient so that descenting material is retained on the item of clothing for several hours.

31. The method of claim 26 wherein the game animal does not sense the hunter when the hunter is a distance from the game animal.

32. The method of claim 31 wherein the distance from the game animal is one of 5 feet, 8 yards, and 10 yards.

33. The method of claim 26 wherein the item of clothing has a color and the ozone changes the color of at least part of the item of clothing.

34. A method of eliminating scent, comprising:
providing an ozone generator to generate a flow of ozone;
directing the flow of ozone into an unenclosed area to create a downwind zone of ozone, the downwind ozone zone being positioned between a hunter, clothing worn by the hunter, and hunting equipment used by the hunter and a game animal located in the unenclosed area, the hunter, the clothing, and the hunting equipment giving off foreign scent that is foreign to the unenclosed area;
the downwind ozone zone eliminating foreign scent in the unenclosed area otherwise detectable by the game animal.

35. The method of claim 34, further comprising positioning the ozone generator upwind of the hunter, and positioning the hunter upwind of the game animal.

36. The method of claim 34, further comprising directing the flow of ozone directly onto at least a portion of one of the hunter, the clothing worn by the hunter, and the equipment used by the hunter.

37. The method of claim 34, further comprising extending the zone to at least partially surround the hunter.

38. The method of claim 34, further comprising positioning the device downwind of the hunter at a location spaced between the hunter and the game animal.

* * * * *